(12) United States Patent
Lopez

(10) Patent No.: US 8,252,349 B2
(45) Date of Patent: Aug. 28, 2012

(54) MILK FEVER

(75) Inventor: Javier Martin-Tereso Lopez, Nijmegen (NL)

(73) Assignee: Nutreco Nederland B.V., Boxmeer (NL)

( * ) Notice: Subject to any disclaimer, the term of this patent is extended or adjusted under 35 U.S.C. 154(b) by 789 days.

(21) Appl. No.: 12/304,414

(22) PCT Filed: Jun. 14, 2007

(86) PCT No.: PCT/NL2007/050282
§ 371 (c)(1),
(2), (4) Date: Feb. 10, 2009

(87) PCT Pub. No.: WO2007/145519
PCT Pub. Date: Dec. 21, 2007

(65) Prior Publication Data
US 2009/0202671 A1    Aug. 13, 2009

(30) Foreign Application Priority Data
Jun. 14, 2006    (EP) .................................... 06076233

(51) Int. Cl.
*A23K 1/18* (2006.01)
*A23K 1/175* (2006.01)
(52) U.S. Cl. .............................. 426/2; 426/635; 426/807
(58) Field of Classification Search .............. 426/2, 635, 426/807
See application file for complete search history.

(56) References Cited

U.S. PATENT DOCUMENTS

| | | | |
|---|---|---|---|
| 4,929,438 A * | 5/1990 | Sawai et al. .................... | 514/143 |
| 6,106,871 A * | 8/2000 | Miller .............................. | 426/2 |
| 6,890,550 B1 | 5/2005 | Jorgensen | |

OTHER PUBLICATIONS

Baumont, r. "Paltability and feeding behavior in ruminants. Areview", Ann Zootech (1996), vol. 45, pp. 385-400.*
"Nutrients influence Palatability", downloaded from http://extension.usu.edu/files/publications/factsheet/1_3_2.pdf, 2 pages, 2004.*
Siener, et al., A Calcium-binding capacities of different brans under simulated gastrointestinal pH conditions. In vitro study with (45)Ca, Journal of agricultural and food chemistry, 2001, vol. 49(9), pp. 4397-4401.
Nelson, et al., The calcium binding properties of natural phytate in chick diets, Nutrition Reports International, 1987, vol. 35(5), pp. 949-956.
Ohkawa, et al., Rice bran treatment for patients with hypercalciuric stones: experimental and clinical studies, Journal of Urology, 1984, vol. 132(6), pp. 1140-1145.
Park, et al., Formaldehyde treatment suppresses ruminal degradation of phytate in soyabean meal and rapeseed meal, British Journal of Nutrition, 1999, vol. 81(6), 467-471.
Konishi, et al., Heat treatment of soybean meal and rapeseed meal suppresses rumen degradation of phytate phosphorus in sheep, Animal Feed Science and Technology, 1999, vol. 80(2), pp. 115-122.
F. D. Goffman, et al., Relationship Between Hydrolytic Rancidity, Oil . . . , Cereal Chem., vol. 80, pp. 689-692, 2003.

* cited by examiner

*Primary Examiner* — Chhaya Sayala
(74) *Attorney, Agent, or Firm* — Lucas & Mercanti, LLP

(57) ABSTRACT

The invention relates to a ruminant feed supplement for the treatment of milk fever. According to the invention rice bran that has been subjected to a ruminal bypass treatment is used in the feed of dairy cows.

The ruminal bypass treatment may for instance be selected from the chemical cross-linking, physical cross-linking, coating, or combinations thereof.

The invention further relates to the use of rice bran for the manufacture of a composition for the prophylactic treatment of parturient paresis in ruminants, wherein the rice bran has been subjected to a ruminal bypass treatment.

10 Claims, No Drawings

MILK FEVER

The invention relates to a ruminant feed supplement that can be used in avoiding milk fever in animals, in particular in farm animals.

Milk fever (parturient paresis) is a disorder of calcium homeostasis. Ruminants, such as dairy cows, often suffer from this disorder in the last days of gestation and in early lactation.

During lactation the demand for calcium is high, which leaves the cow in a negative calcium balance. This negative calcium balance activates the vitamin D-dependent complex mechanisms which actively increase the utilisation of the dietary calcium by increasing absorption from the digestive tract and by resorbing calcium from the skeletal system via the blood. These active mechanisms allow for a covering of up to 80% of the demand for calcium during lactation. Hence, these mechanisms normally prevent the occurrence of hypocalcaemia.

During the two months immediately prior to calving, calcium requirement is at a minimum. Normally, during this period dairy cows are not milked, and there is no calcium requirement for lactation. Therefore, in the period prior to calving the dairy cow has a low demand for calcium, and is able to absorb sufficient calcium via the digestive tract by simple passive diffusion. The act of calving induces lactation and milk production is at a peak by 4-6 weeks thereafter. The onset of lactation however corresponds with a sudden high calcium demand for milk production. The calcium regulating mechanisms are not always prepared for this sudden demand for calcium and hence hypocalcaemia and milk fever may occur.

The prior art proposes several treatments for the prevention of milk fever in ruminants. In general, a low calcium strategy has shown to be the most effective. Such a strategy intends to promote the active mechanism of calcium absorption before calving. Oral calcium drenching around calving was found to be effective in prevention of milk fever, but some drenches were shown to cause lesions in the forestomachs. Feeding rations with a negative dietary cation-anion difference (measured as (Na+K)−(Cl+S)) also showed significant reduction of milk fever incidence, but this treatment suffers from a palatability problem. Feeding rations low in calcium appears to be highly efficient in milk fever prevention provided that the calcium intake in the dry period (the period in which the dairy cow is not lactating) is kept below 20 g per day. The main problem in implementing this treatment is a difficulty in formulating rations sufficiently low in calcium when using commonly available feeds (Thilsing-Hansen *Acta Veterinaria Scandinavica* 2002, 43, 1-19).

WO-A-00/56167 describes a method of preventing hypocalcaemia in lactating animals comprising administering to the animal during at least part of the dry period an effective amount of a compound which reduces absorption of calcium from drinking water and/or from the ration of said animal. According to this publication, the preferred compound for reducing calcium absorption is a clay mineral, such as a zeolite. In order to be effective the clay mineral needs to be administered in large amounts of up to 1 000 g per day per animal, which in practise causes palatability problems.

Object of the present invention is to provide a ruminant feed supplement for reducing intestinal calcium absorption, which feed supplement has a high palatability and acceptance, and at the same time efficiently binds calcium in the duodenum.

It has been found that this object can be met by a ruminant feed supplement comprising specifically modified rice bran.

Thus, in a first aspect the present invention is directed to a ruminant feed supplement comprising rice bran, wherein the rice bran has been subjected to a ruminal bypass treatment.

In the context of the present invention the term "rice bran" is meant to include rice bran, rice hulls, rise polishings, rice shorts, rice bran solvent extract, stabilised rice bran, and any other byproduct form rice processing that contains a sufficient amount of phytic acid, in particular more than 1 wt. %.

Rice bran comprises a large amount of phytic acid. In the context of this invention the term "phytic acid" is meant to include inositol monophosphate, inositol diphosphate, inositol triphosphate, inositol tetraphosphate, inositol pentaphosphate, inositol hexaphosphate and mixtures thereof. Phytic acid is the principal storage form of phosphorus in many plant tissues, especially seeds. Normally, phytic acid is digested in the first stomach of ruminants by phytase enzyme activity and is one of the main sources of phosphorus for the animals. Ruminal microbes provide phytase enzyme to cut off the phosphates groups of the molecule to cover the need for phosphorus. However, the calcium binding properties of the molecule are thereby removed before it reaches the duodenum.

When the rice bran is treated with a ruminal bypass treatment, the phytic acid is able to reach the duodenum where it is effective as a strong calcium absorption antagonist, since each of the phosphate groups in phytic acid can bind a calcium ion.

Moreover, the inventors found that although phytic acid is probably an important active calcium binding ingredient of rice bran, it is not the only active compound for this purpose in the product. Therefore, the use of rice bran is particularly interesting, especially since rice bran does not present palatability problems.

The use of rice bran may have other beneficial dietary advantages when applied in mammals, such as general improvement of lipid metabolism, improvement of oxidative status and positive effects on prevention of hypertension, hyperlipidemia, and/or hyperglycemia.

By treating the rice bran with a ruminal bypass treatment, calcium absorption in the duodenum can effectively be reduced and a negative calcium balance may be obtained which is effective in the prevention of milk fever (parturient paresis).

In principle, any ruminal bypass treatment known in the art may be used such as coating, chemical cross-linking with species such as aldehydes (for example formaldehyde), tannins and/or any other protein binding products, or physical cross-linking such as heat treatment. Naturally, the invention also includes combinations of bypass treatments.

The best results have been obtained with rice bran that has been subjected to chemical cross-linking or to a heat treatment.

It is preferred that the phytic acid in the ruminal bypass treated rice bran does not degrade until in the duodenum. In a preferred embodiment at least 25 wt %, preferably above 40 wt % and most preferably above 50 wt % of the phytic acid in the ruminal bypass treated rice bran of the feed supplement of the invention remains intact until in the duodenum. More preferably at least 75 wt % of the phytic acid remains intact until in the duodenum.

Chemical cross-linking of the rice bran can for instance be achieved by treatment with formaldehyde or other cross-linking agents. Typically the treatment comprises the application of about 0.5-1.0 g of formaldehyde per 100 g of protein in the product, preferably about 0.8 g of formaldehyde per 100 g of protein in the product. Treatment with formaldehyde is preferred, because it is accepted in animal feed processing.

In a heat treatment, the rice bran is typically brought to a temperature of above 115° C., preferably above 125° C. Irreversible degradation of the active ingredients occurs at a temperature of above 135° C. Therefore, the heat treatment is preferably carried out at a temperature of 115-130° C. Normally, good results are obtained when the heat treatment is carried out for 2-30 minutes depending on the pressure applied. A typical heat treatment is a heating step to 120° C. for 2 minutes.

The rice bran of the present invention preferably comprises at least 2 wt. % of phytic acid, with respect to the weight of rice bran, more preferably at least 6 wt. %.

Preferably a ruminant ration which comprises the feed supplement according to the invention contains up to 30 wt. % of ruminal bypass treated rice bran, with respect to the weight of the total ration, preferably up to 25 wt. %, and more preferably up to 20 wt. %, e.g. 1-15 wt. %. When the feed comprises more than 30 wt. % of ruminal bypass treated rice bran, the nutritional characteristics of the ration may be compromised. Therefore, the amount of ruminal bypass treated rice bran is most preferably from 1 wt. % to 30 wt. %.

By way of example, for a typical feeding application the following typical figures may apply. A cow before calving will generally eat between 10 and 13 kg/day of dry matter feed. The majority of it will be forage. Normally between 1 and 4-5 kg of concentrates are fed. That concentrate supplement may typically comprise about one half to one third of the supplement of the present invention.

Suitable ruminants that can be employed in accordance with the present invention include cattle, sheep, goats, llamas, deer, or antelope. The amount of concentrate supplement to be fed to each of these animals mainly depends on bodyweight and typically corresponds to the figures mentioned above for cows, corrected for the bodyweight of the specific animal species.

The feed supplement may further comprise other ingredients such as flavouring agents, organic trace elements, minerals and vitamins and sources of glycogenic energy.

In a further aspect, the present invention also relates to the use of rice bran for the manufacture of a medicament for treating parturient paresis in ruminants, wherein the rice bran is treated with a ruminal bypass treatment.

The bypass fraction of phytic acid in rice bran can be increased by various methods. Table 1 illustrates the results obtained with the in sacco technique on a rice bran sample treated to make phytic acid rumen bypass through physical coating with saturated fat. For this specific product the bypass fraction of phytic acid was estimated to be between 26 and 34 wt. % of the original content of the bran.

TABLE 1

Degradation parameters of dry matter (DM) and phytic acid and estimates of bypass fractions

| | Soluble fraction | Undegradable fraction | Degradable fraction | Degradation rate, $k_d$[1] (%/h) | % Bypass fraction $k_p$[2] = 0.04%/h | $k_p$[2] = 0.06%/h |
|---|---|---|---|---|---|---|
| DM | 15.2 | 10.7 | 74.1 | 0.041 | 47.2 | 54.6 |
| Phytic acid | 4.0 | 4.0 | 92.0 | 0.125 | 26.3 | 33.9 |

[1] $k_d$ = ruminal degradation rate
[2] $k_p$ = ruminal passage rate

Feeding rumen protected rice bran can change calcium balance and stimulate calcium homeostasis. In one trial, the product described in Table 1 was fed to nine pregnant non lactating Holstein cows at the Nutreco Ruminant Research Centre (Boxmeer, The Netherlands). The cows received 2000 g of product for a week, after having been monitored for one week. Thereafter they were observed for another week after the end of supplementation. The treatment produced a significant decrease in urinary calcium showing that calcium homeostatic mechanisms were triggered by the supplementation. The withdrawal of the treatment produced an increase in calcium excretion beyond the initial levels suggesting that calcium absorption had been up-regulated by the treatment (Table 2).

TABLE 2

Differences among least-square means for calcium balance indicators

| | $1^{st}$ period | $2^{nd}$ period | $3^{rd}$ period |
|---|---|---|---|
| Ca intake | a 47.2 | B 33.9 | c 43.0 |
| Urine Ca/creatinine | a 0.51 | B 0.15 | c 1.12 |
| Urine pH | Aa 8.46 | B 8.40 | Ba 8.50 |
| Urine Ca/creatinine/Ca intake | a 0.01067 | A 0.00540 | b 0.02593 |

Differences in capital letters indicate $p < 0.05$, differences in lower case letters indicates $p < 0.01$

The invention claimed is:

1. A ruminant feed supplement comprising a protected rice bran, wherein the rice bran has been subjected to a ruminal bypass treatment to inhibit degradation of phytic acid contained therein.

2. The ruminant feed supplement according to claim 1, wherein the ruminal bypass treatment is selected from the group consisting of chemical cross-linking, physical cross-linking, coating, and combinations thereof.

3. The ruminant feed supplement according to claim 2, wherein the chemical cross-linking is a cross-linking with an aldehyde, or a tannin.

4. The ruminant feed supplement according to claim 2, wherein the physical cross-linking is a cross-linking by a heat treatment.

5. The ruminant feed supplement according to claim 1, further comprising a clay-mineral.

6. The ruminant feed supplement according to claim 1, wherein the ruminal bypass treated rice bran comprises at least 3 wt. % of phytic acid.

7. The ruminant feed comprising a feed supplement according to claim 1, wherein the amount of the ruminal bypass treated rice bran in the feed is less than 40 wt. % with respect to the total amount of feed.

8. The ruminant feed according to claim 7, wherein the amount of the ruminal bypass treated rice bran in the feed is less than 35 wt. %.

9. The ruminant feed according to claim 7, wherein the amount of the ruminal bypass treated rice bran in the feed is 1-25 wt. %.

10. A method of preventing parturient paresis in ruminants, comprising feeding a sufficient amount of the ruminant feed supplement of claim 1 to a ruminant in need thereof.

* * * * *